US012624178B2

(12) United States Patent (10) Patent No.: US 12,624,178 B2
Chen et al. (45) Date of Patent: May 12, 2026

(54) MANUFACTURING METHOD OF A MODIFIED POLYMER LAYER MODIFIED BY HYDROXYAPATITE

(71) Applicant: TAIWAN TEXTILE RESEARCH INSTITUTE, New Taipei City (TW)

(72) Inventors: Wei-Yu Chen, New Taipei City (TW); Jui-Sheng Lee, New Taipei City (TW); Hui-Ju Hsu, New Taipei City (TW)

(73) Assignee: TAIWAN TEXTILE RESEARCH INSTITUTE, New Taipei City (TW)

( * ) Notice: Subject to any disclaimer, the term of this patent is extended or adjusted under 35 U.S.C. 154(b) by 439 days.

(21) Appl. No.: 18/332,045

(22) Filed: Jun. 9, 2023

(65) Prior Publication Data

US 2024/0141123 A1 May 2, 2024

(30) Foreign Application Priority Data

Oct. 27, 2022 (TW) .................................. 111140963

(51) Int. Cl.
| | |
|---|---|
| *C08J 7/14* | (2006.01) |
| *A61L 27/28* | (2006.01) |
| *A61L 27/30* | (2006.01) |
| *A61L 27/32* | (2006.01) |
| *A61L 27/34* | (2006.01) |
| *A61L 27/50* | (2006.01) |
| *B01J 19/08* | (2006.01) |
| *C08J 7/06* | (2006.01) |
| *C08J 7/18* | (2006.01) |

(52) U.S. Cl.
CPC ................. *C08J 7/14* (2013.01); *A61L 27/28* (2013.01); *A61L 27/306* (2013.01); *A61L 27/32* (2013.01); *A61L 27/34* (2013.01); *A61L 27/50* (2013.01); *B01J 19/088* (2013.01); *C08J 7/06* (2013.01); *C08J 7/18* (2013.01); *A61L 2400/18* (2013.01); *A61L 2420/02* (2013.01); *A61L 2420/04* (2013.01); *A61L 2430/10* (2013.01); *B01J 2219/0896* (2013.01); *C08J 2367/02* (2013.01); *C08J 2433/02* (2013.01)

(58) Field of Classification Search
CPC ... C08J 7/14; C08J 7/18; C08J 2367/02; C08J 2433/02; C08J 7/06; A61L 27/32; A61L 27/28; A61L 27/306; A61L 27/34; A61L 27/50; A61L 2400/18; A61L 2420/02; A61L 2420/04; A61L 2430/10; B01J 19/088; B01J 2219/0896
See application file for complete search history.

(56) References Cited

U.S. PATENT DOCUMENTS

2008/0262631 A1 10/2008 Jansen et al.

FOREIGN PATENT DOCUMENTS

| | | |
|---|---|---|
| CN | 105641741 A | 6/2016 |
| JP | 3051927 B1 * | 6/2000 |
| TW | 110146145 | 12/2021 |

* cited by examiner

*Primary Examiner* — Rabon A Sergent
(74) *Attorney, Agent, or Firm* — McClure, Qualey & Rodack, LLP

(57) ABSTRACT

A manufacturing method of a modified polymer layer modified by hydroxyapatite is provided in the present disclosure, including following steps: (a) providing a polymer layer; (b) plasma-activating acrylic acid using an atmospheric cold plasma device to modify a surface of the polymer layer to obtain an acrylic-modified polymer layer; (c) immersing the acrylic-modified polymer layer in a first solution containing a calcium ion to obtain a calcium-containing modified layer; and (d) immersing the calcium-containing modified layer in a second solution containing phosphate salt to obtain a modified polymer layer modified by hydroxyapatite.

10 Claims, 5 Drawing Sheets

100

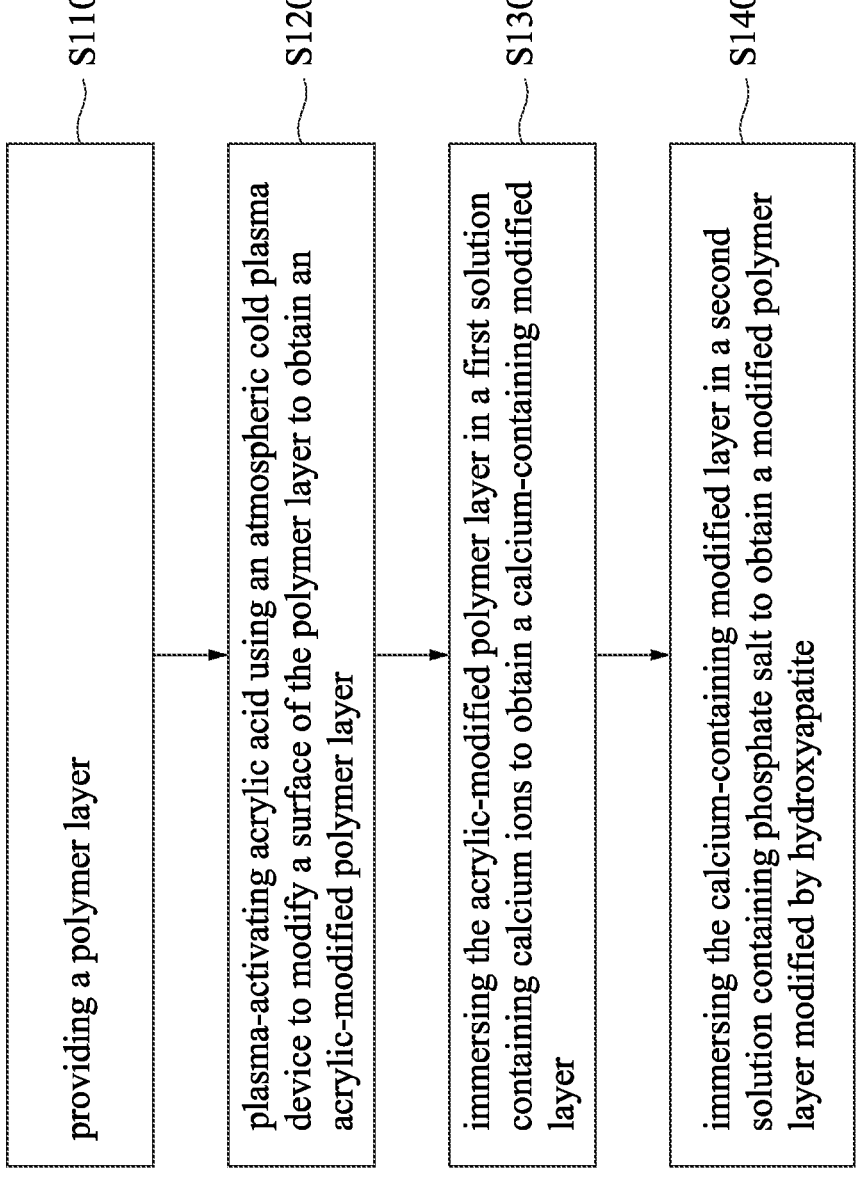

providing a polymer layer ⟶ S110 plasma-activating acrylic acid using an atmospheric cold plasma device to modify a surface of the polymer layer to obtain an acrylic-modified polymer layer ⟶ S120 immersing the acrylic-modified polymer layer in a first solution containing calcium ions to obtain a calcium-containing modified layer ⟶ S130 immersing the calcium-containing modified layer in a second solution containing phosphate salt to obtain a modified polymer layer modified by hydroxyapatite ⟶ S140

Fig. 1

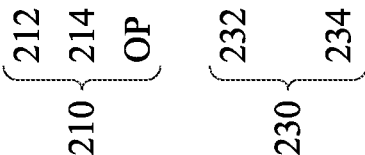
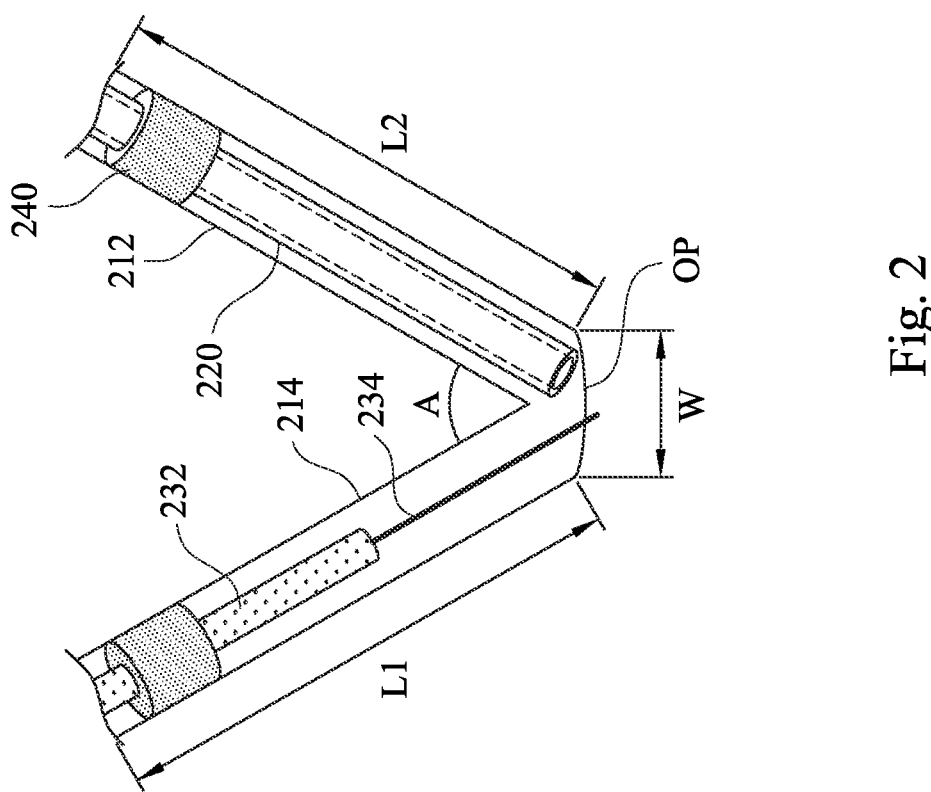
Fig. 2

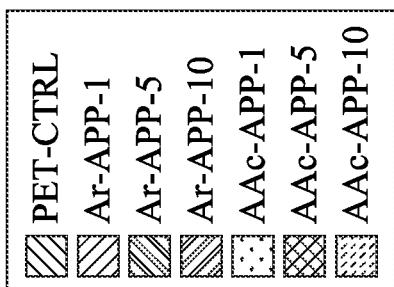
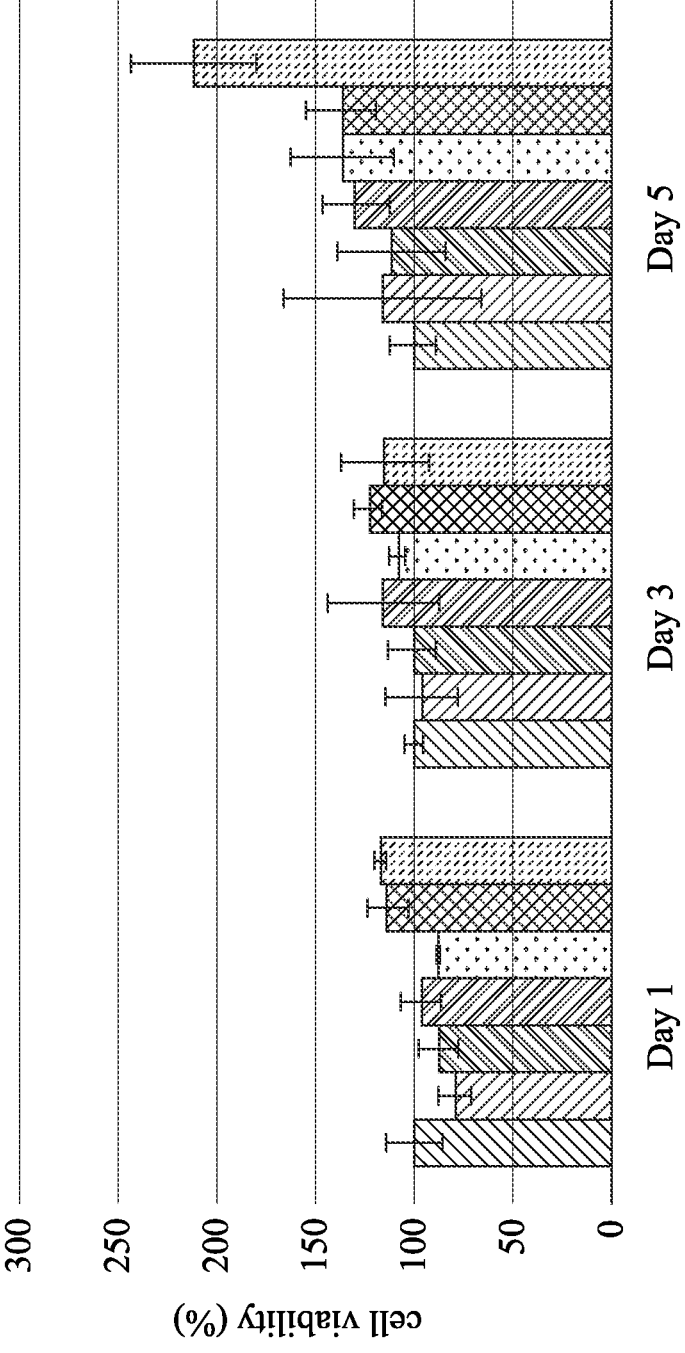
Fig. 3C

MANUFACTURING METHOD OF A MODIFIED POLYMER LAYER MODIFIED BY HYDROXYAPATITE

CROSS-REFERENCE TO RELATED APPLICATION

This application claims priority to Taiwan Application Serial Number 111140963, filed Oct. 27, 2022, which is herein incorporated by reference.

BACKGROUND

Field of Invention

The present disclosure relates to a manufacturing method of a modified polymer layer. In particular, the present disclosure is related to a manufacturing method of a modified polymer layer modified by hydroxyapatite.

Description of Related Art

Along with the aggravation of aging trend, the number of the patients with joint injury or bone injury constantly increases. Therefore, the performance requirements for medical implant materials (usually including polymers, such as artificial ligaments prepared from polyethylene terephthalate) have also increased. However, the current artificial ligament materials usually have a hydrophobic surface, which has poor biocompatibility and is unfavorable for cell attachment.

Therefore, how to improve the hydrophilicity and biocompatibility of the artificial ligament materials is a problem to be solved.

SUMMARY

A manufacturing method of a modified polymer layer modified by hydroxyapatite is provided in the present disclosure, including following steps: providing a polymer layer; plasma-activating acrylic acid using an atmospheric cold plasma device to modify a surface of the polymer layer to obtain an acrylic-modified polymer layer; immersing the acrylic-modified polymer layer in a first solution containing calcium ions to obtain a calcium-containing modified layer; and immersing the calcium-containing modified layer in a second solution containing phosphate salt to obtain a modified polymer layer modified by the hydroxyapatite. Functionalization of the polymer layer via the atmospheric cold plasma device decreases manufacturing time, reduces damage to the polymer layer and improves modification efficiency of the hydroxyapatite deposition.

According to an embodiment of the present disclosure, the step (b) includes introducing the acrylic acid and argon gas into a hollow metal electrode accommodated in a first hollow element of a V-shaped hollow tube, thereby generating an acrylic acid plasma from a bottom opening of the V-shaped hollow tube to modify the surface of the polymer layer.

According to an embodiment of the present disclosure, the step (b) further includes modifying the surface of the polymer layer by using a needle-shaped metal electrode accommodated in a second hollow element of the V-shaped hollow tube, in which the first hollow element intersects with the second hollow element to form the bottom opening.

According to an embodiment of the present disclosure, the step (b) includes plasma-activating the acrylic acid at a temperature of from 25° C. to 70° C.

According to an embodiment of the present disclosure, the step (b) includes plasma-activating the acrylic acid with a current of from $10^{-5}$ A to 1 A.

According to an embodiment of the present disclosure, the step (b) includes modifying the surface of the polymer layer for 0.5 s to 20 s.

According to an embodiment of the present disclosure, in the step (c), a concentration of the calcium ion in the first solution is from 0.1 M to 0.5 M, and a concentration of the phosphate salt in the second solution is from 0.05 M to 0.3 M.

According to an embodiment of the present disclosure, the first solution in the step (c) is calcium nitrate tetrahydrate solution, and the second solution in the step (d) is diammonium hydrogen phosphate solution.

According to an embodiment of the present disclosure, an immersion time of the step (c) or the step (d) is from 0.25 hr to 1 hr.

According to an embodiment of the present disclosure, the manufacturing method further includes repeating the step (c) and the step (d), in which the modified polymer layer is alternately immersed in the first solution and the second solution for 1 cycle to 5 cycles.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 1 depicts a flowchart of a method of manufacturing a modified polymer layer modified by hydroxyapatite.

FIG. 2 depicts a cross-sectional view of a plasma treatment zone of an atmospheric cold plasma device.

FIG. 3C depicts a tendency figure of cell viability of the polymer layer or the modified polymer layers obtained by the different manufacturing conditions when co-cultured with osteoprogenitor cells for different days.

DETAILED DESCRIPTION

Figure 3A:
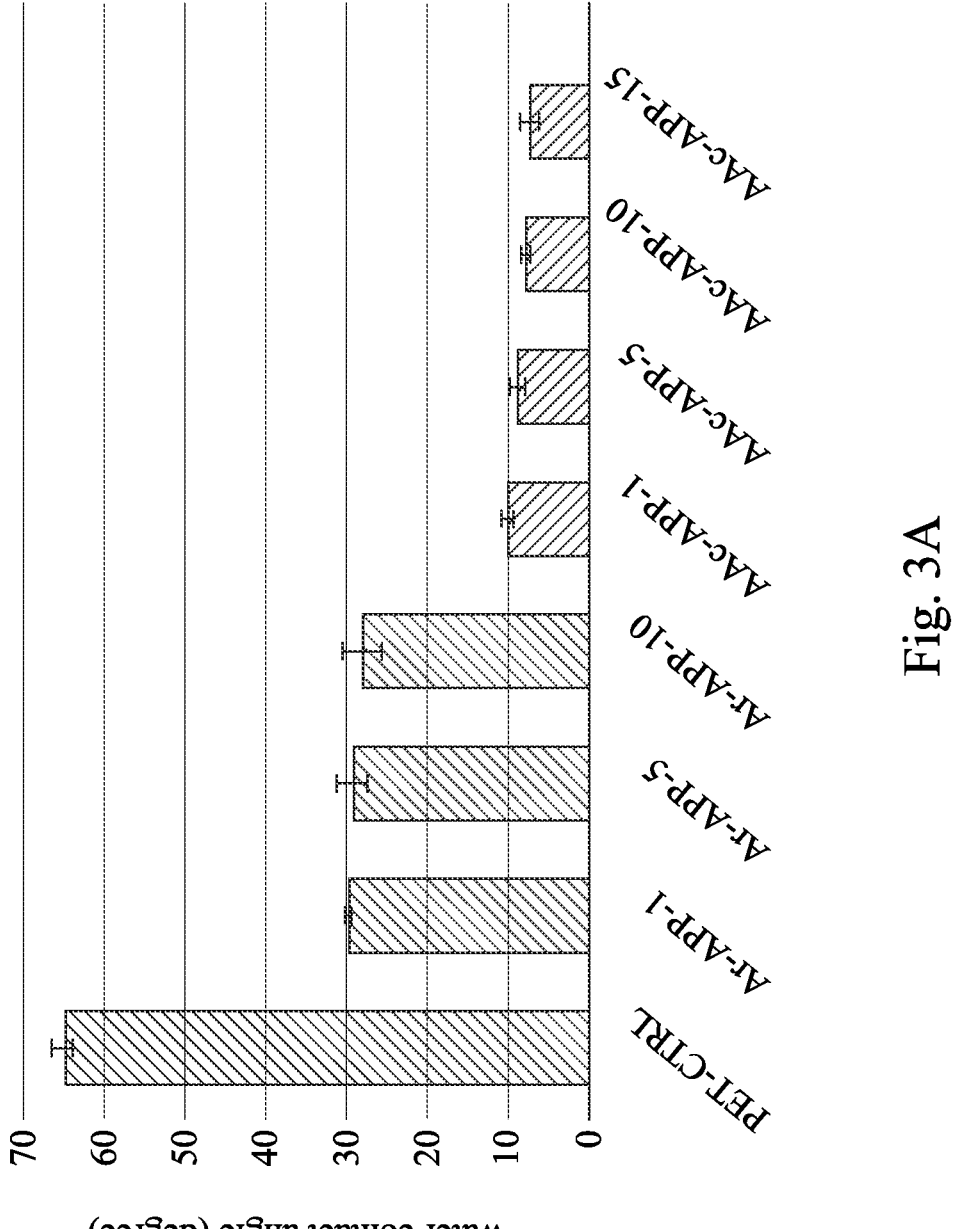
FIG. 3A depicts a comparison figure of contact angles between a modified polymer layer and modified polymer layers obtained by different manufacturing conditions.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The device may be otherwise oriented (rotated 90 degrees or at other orientations) and the spatially relative descriptors used herein may likewise be interpreted accordingly.

As used herein, "polymer" refers to a long-chain molecule composed of small molecular monomers connected continuously by covalent bonds, usually with a molecular weight greater than 10,000.

The present disclosure provides a manufacturing method of a modified polymer layer modified by hydroxyapatite ($Ca_{10}(PO_4)_6(OH)_2$), including plasma-activating acrylic acid using an atmospheric cold plasma device to modify a surface of the polymer layer. The use of the atmospheric cold plasma device not only eliminates the need for vacuum-pumping related components and steps, which can save manufacturing costs and time, but also can be performed at room temperature without causing damage to the polymer layer. In addition, the modification efficiency of hydroxyapatite on the surface of the modified polymer layer can be improved by using the acrylic plasma to modify the surface of the polymer layer.

Please refer to FIG. 1, an embodiment of the present disclosure depicts a flowchart of a manufacturing method 100 of manufacturing a modified polymer layer modified by hydroxyapatite, in which the manufacturing method 100 includes step S110 to step S140.

Step S110 refers to (a) providing a polymer layer.

In some embodiments, the material of the polymer layer is polyester, such as polyethylene terephthalate.

Step S110 refers to plasma-activating acrylic acid using an atmospheric cold plasma device to modify the surface of a polymer layer to obtain an acrylic-modified polymer layer.

Plasma-activating acrylic acid by the atmospheric cold plasma device eliminates the need for vacuum-pumping related components and steps, which can save manufacturing costs and time. In addition, compared with high-temperature treatment of a thermal plasma device (such as arc discharge with a processing temperature from 800° C. to 1200° C.), the atmospheric cold plasma device can be performed at room temperature, and the polymer layer is not required to withstand high-temperature treatment, which causes less damage to the polymer layer.

In addition, compared with activation of the polymer layer using other types of plasma gases (for example, providing the surface with oxygen radicals or hydrogen peroxide), the polymer layer modified by acrylic acid has higher stability and is less prone to reacting with water and oxygen in the air. Therefore, the polymer layer modified by acrylic acid can improve the reaction efficiency of subsequent hydroxyapatite modification on the surface of the modified polymer layer, thereby increasing the density of hydroxyapatite.

In some embodiments, step S120 includes performing plasma-activation on acrylic acid at 0.5 atmosphere to 1.5 atmospheres (for example, 1 atmosphere).

In some embodiments, step S120 includes performing plasma activation on acrylic acid using glow discharge. For example, acrylic acid is plasma-activated at a current of from $10^{-5}$ A to 1 A (for example, $10^{-5}$ A, $10^{-4}$ A, $10^{-3}$ A, $10^{-2}$ A, $10^{-1}$ A, 1 A, or any value between the foregoing intervals).

It can be understood that compared with arc discharge (commonly known as thermal plasma), which emits a large amount of heat energy, glow discharge emits lower heat energy so as to plasma-activate acrylic acid at a lower temperature. Specifically, acrylic acid can be plasma-activated at a temperature of from 25° C. to 70° C. (for example, the temperature is 25° C., 30° C., 40° C., 50° C., 60° C., 70° C., or any value between the foregoing intervals). If the temperature is too high, the polymer layer will be damaged. If the temperature is too low, the efficiency of plasma-activation of acrylic acid will be poor.

In some embodiments, step 120 includes performing modifying the surface of the polymer layer for 0.5 s to 20 s (for example, 0.5 s, 1 s, 2 s, 3 s, 4 s, 5 s, 6 s, 7 s, 8 s, 9 s, 10 s, 11 s, 12 s, 13 s, 14 s, 15 s, 16 s, 17 s, 18 s, 19 s, 20 s, or any value between the foregoing intervals).

It is worth noting that, along with the number of seconds from 0.5 to 10, the efficiency of surface modification can be improved, and the hydrophilicity of the modified polymer layer obtained in the follow steps can be further increased. In addition, the modified polymer layer obtained by the condition has the best cell viability. However, when the number of seconds is further increased from 10 s (for example, the number of seconds is increased to be 15 s), the hydrophilicity of the subsequently obtained modified polymer layer remains the same and does not continue increasing. Therefore, performing the surface modification on the polymer layer for 10 seconds can obtain the modified polymer layer with the best hydrophilicity and cell viability in a shorter treatment time.

In some embodiments, the atmospheric cold plasma device at step S120 includes a plasma treatment zone 200 as shown in FIG. 2. The plasma treatment zone 200 includes a V-shaped hollow tube 210, a hollow metal electrode 220, a needle-shaped metal electrode 230 and a securing portion 240.

In some embodiments, the V-shaped hollow tube 210 includes a first hollow element 212, a second hollow element 214 and a bottom opening OP formed by the intersection of the first hollow element 212 and a second hollow element 214. An angle A is formed between the first hollow element 212 and the second hollow element 214, and the angle A is an acute angle, for example, between 30 degrees and 75 degrees (such as 30 degrees, 45 degrees, 60 degrees, 75 degrees, or any value between the foregoing intervals), so as to jointly form a downward bottom opening OP at the bottom. In some embodiments, the hollow metal electrode 220 is accommodated in a first hollow element 212 of the V-shaped hollow tube 210. In some embodiments, the needle-shaped metal electrode 230 is accommodated in a second hollow element 214 of the V-shaped hollow tube 210, in which the needle-shaped metal electrode 230 includes a column-shaped extension portion 232 and a needle-shaped discharge portion 234 connect to the column-shaped extension portion 232, in which the needle-shaped discharge portion 234 is adjacent to the bottom opening OP. In some embodiments, the needle-shaped metal electrode 230 protrudes from the V-shaped hollow tube 210, for example, protruding by 0.5 cm, so as to improve the efficiency of the plasma treatment of the polymer layer. In some embodiments, the securing portion 240 fixes the hollow metal electrode 220 and the needle-shaped metal electrode 230 in the first hollow element 212 and the second hollow element 214 respectively.

In some embodiments, the V-shaped hollow tube 210 is a glass tube. In some embodiments, two sides of the V-shaped hollow tube 210 have a length L1 and a length L2, in which the length L1 and the length L2 are 5 cm to 15 cm (for example, 5 cm, 10 cm, 15 cm, or any value between the aforementioned intervals) so as to allow the hollow metal electrode 220 and the needle-shaped metal electrode 230 to be basically fixed and accommodated therein. In some embodiments, the length L1 and the length L2 may be the same or different. In some embodiments, the diameter W of the bottom opening OP is from 0.5 cm to 5 cm (for example, 0.5 cm, 1 cm, 2 cm, 3 cm, 4 cm, 5 cm, or any value between the aforementioned intervals), so that the acrylic plasma can fully act on the surface of the polymer layer.

In some embodiments, step S120 includes introducing acrylic acid and argon gas into the hollow metal electrode 220 accommodated in the first hollow element 212 of the V-shaped hollow tube 210, thereby generating an acrylic acid plasma to modify the surface of the polymer layer from a bottom opening OP of the V-shaped hollow tube 210, in which argon gas is used to introduce acrylic acid into the hollow metal electrode 220. In some embodiments, argon gas of from 2.5 standard liter/minute to 5 standard liter/minute (such as 2.5 standard liter/minute, 3 standard liter/minute, 4 standard liter/minute, 5 standard liter/minute, or any value between the aforementioned intervals) is used to introduce acrylic acid into the hollow metal electrode 220.

In some embodiments, in addition to modifying the surface of the polymer layer from the bottom opening OP of the V-shaped hollow tube 210, step S120 further includes using the needle-shaped metal electrode 230 accommodated in the second hollow element 214 of the V-shaped hollow tube 210 to modify the surface of the polymer layer. By using the hollow metal electrode 220 and the needle-shaped metal electrode 230 at the same time, the efficiency of surface modification on the polymer layer by acrylic acid can be improved.

It is worth emphasizing that, compared with the setting of the electrodes on the upper and lower sides of the polymer layer and performing plasma modification treatment on the polymer layer from the upper and lower sides, the plasma treatment zone 200 allows the hollow metal electrode 220 and needle-shaped metal electrode 230 to face the bottom opening OP together to modify the surface of the polymer layer by accommodating the hollow metal electrode 220 and the needle-shaped metal electrode 230 in the V-shaped hollow tube 210, and the restriction of shape and thickness of the polymer layer can be avoided, so that the selection of the material of the polymer layer has better flexibility.

In some embodiments, the step of generating the acrylic acid plasma to modify the surface of the polymer layer from the bottom opening OP of the V-shaped hollow tube 210 or using the needle-shaped metal electrode 230 accommodated in the second hollow element 214 of the V-shaped hollow tube 210 to modify the surface of the polymer layer includes placing the polymer layer away from the bottom opening OP at a distance in the range of from 0.5 cm to 3 cm (for example, 0.5 cm, 1 cm, 2 cm, 3 cm, or any value between the foregoing intervals) for surface modification, in which the surface modification acquires the best efficiency when the distance is 1 cm.

Step S130 refers to immersing the acrylic-modified polymer layer in the first solution containing the calcium ion to obtain the calcium-containing modified layer. Specifically, through the ionic attraction of carboxylic acid in acrylic acid, the calcium ions can be adsorbed on the surface of the acrylic-modified polymer layer to modify the acrylic-modified polymer layer.

In some embodiments, a concentration of the calcium ion in the first solution at step S130 is from 0.1 M to 0.5 M, such as 0.1 M, 0.2 M, 0.3 M, 0.4 M, 0.5 M or any value between the foregoing intervals. If the concentration of the calcium ions is too low, the calcium modification efficiency will be poor. If the concentration of the calcium ions is too high, the increase of the modification efficiency will be limited, but the cost will increase. In some embodiments, the first solution is calcium nitrate tetrahydrate solution. In some embodiments, the immersion time is from 0.25 hr to 1 hr, such as 0.25 hr, 0.5 hr, 0.75 hr, 1 hr, or any value between the foregoing intervals. If the immersion time is too short, the modification efficiency of the calcium ion is poor. If the immersion time is too long, the increase of the modification efficiency will be limited, but the reaction time will increase.

Step S140 refers to immersing the calcium-containing modified layer in a second solution containing phosphate salt to obtain a modified polymer layer modified by hydroxyapatite.

In some embodiments, phosphate salt includes phosphate radical, hydrogen phosphate radical, dihydrogen phosphate radical, or a combination of the foregoing. Through the ionic attraction of the calcium ions, phosphate radical, hydrogen phosphate radical, dihydrogen phosphate radical, or a combination of the foregoing can be adsorbed on the surface of the calcium-containing modified layer, thereby forming the modified polymer layer modified by hydroxyapatite.

In some embodiments, a concentration of phosphate salt in the second solution of step S140 is from 0.05 M to 0.3 M, such as 0.05 M, 0.1 M, 0.2 M, 0.3 M, or any value between the foregoing intervals. If the concentration of phosphate salt is too low, the modification efficiency of phosphate salt is poor. If the concentration of phosphate salt is too high, the increase of the modification efficiency will be limited, but the cost will increase. In some embodiments, the second solution is diammonium hydrogen phosphate solution. In some embodiments, the immersion time is from 0.25 hr to 1 hr, such as 0.25 hr, 0.5 hr, 0.75 hr, 1 hr, or any value between the foregoing intervals. If the immersion time is too short, the modification efficiency of phosphate salt is poor. If the immersion time is too long, the increase of the modification efficiency will be limited, but the reaction time will increase.

In some embodiments, the manufacturing method 100 further includes repeating step S130 and step S140, in which the modified polymer layer is alternately immersed in the first solution and the second solution for 1 cycle to 5 cycles, such as 1 cycle, 2 cycles, 3 cycles, 4 cycles, or 5 cycles. It is worth emphasizing that, compared with the use of only argon to modify the polymer layer (generating oxygen radicals on the surface), acrylic acid is chosen to modify the surface of the polymer layer in step S120, which can improve the modification efficiency of the calcium ions in the step S130, further increasing the modification efficiency of phosphate salt in the step S140. Therefore, the cycle number required by step S130 and step S140 can be decreased, and the time required by the reaction of the manufacturing method 100 can be decreased.

In the following description, multiple examples of the present disclosure will be recited to carry out various analysis to verify the efficacy of the present disclosure.

Example 1. Surface Hydrophilicity and Surface Stability Test of Modified Polymer Layer Modified by Hydroxyapatite 1. Manufacturing Method of Modified Polymer Layer Modified by Hydroxyapatite First, acrylic acid was plasma-activated using an atmospheric cold plasma device, in which the atmospheric cold plasma device included a plasma treatment zone 200 as shown in FIG. 2. Specifically, at room temperature (about 25° C.), 4 standard liters/minute of argon gas was used to introduce acrylic acid into the hollow metal electrode 220, and acrylic acid was plasma-activated using the hollow metal electrode 220 and the needle-shaped metal electrode 230 under the condition of a voltage of 2400 volts and a current of 25 mA, thereby generating acrylic plasma in the bottom opening OP.

Furthermore, the polymer layer (polyethylene terephthalate was used as the material in the series of examples) was placed at 1 cm away from the bottom opening OP of the V-shaped hollow tube 210, and acrylic acid was used to perform surface modification treatment on the polymer layer for 1 s, 5 s, 10 s or 15 s to obtain a polymer layer surface-modified by acrylic acid (acrylic-modified polymer layer).

Furthermore, after immersing the acrylic-modified polymer layer in calcium nitrate tetrahydrate solution of 0.3 M for 0.5 hour, the acrylic-modified polymer layer was further immersed in diammonium hydrogen phosphate solution of 0.18 M for 0.5 hr, and 2 cycles of the above mentioned procedures were performed (this step was briefly referred to as an alternative immersion method in the following description), so that hydroxyapatite was deposited on the surface of the acrylic-modified polymer layer to obtain a modified polymer layer modified by hydroxyapatite, and a calcium-phosphorus ratio was about 1.50 to 1.87.

2. Surface Hydrophilicity Test

As the manufacturing method of the point 1 mentioned above, according to the manufacturing condition of the following Table 1, the modified polymer layers treated with different plasma gases (only argon or acrylic acid) and different processing time (1 s, 5 s, 10 s and 15 s) were obtained. Then, the sessile drop method was performed, in which 3 μL water was added to each surface to be tested, and the water contact angle was measured with a microscope. The surface hydrophilicity could be determined by the water contact angle. The smaller the water contact angle represented, the better hydrophilicity the modified polymer layer had. Please refer to FIG. 3A, demonstrating the result of each group that the value was calculated after three repeated times.

TABLE 1

| Group | Name | Treatment Time of Argon Plasma (s) | Treatment Time of Acrylic Acid Plasma (s) | Alternative Immersion Method |
|---|---|---|---|---|
| Comparison | PET-CTRL | — | — | — |
| | Ar-APP-1 | 1 | — | V |
| | Ar-APP-5 | 5 | — | — |
| | Ar-APP-10 | 10 | — | — |

TABLE 1-continued

| Group | Name | Treatment Time of Argon Plasma (s) | Treatment Time of Acrylic Acid Plasma (s) | Alternative Immersion Method |
|---|---|---|---|---|
| Example | AAc-APP-1 | — | 1 | V |
| | AAc-APP-5 | — | 5 | V |
| | AAc-APP-10 | — | 10 | V |
| | AAc-APP-15 | — | 15 | V |

Note:
The difference of groups of Ar-APP-1, Ar-APP-5, Ar-APP-10 and Ar-APP-10 and groups of AAc-APP-1, AAc-APP-5, AAc-APP-10 and AAc-APP-15 was that group Ar only used Ar gas without introduction of acrylic acid. As for the conditions of voltage and current, all groups were the same.

FIG. 3A demonstrated that PET-CTRL group (the group without any treatment) had the lowest hydrophilicity; Ar-APP-1, Ar-APP-5 and Ar-APP-10 groups (the groups only treated with argon plasma) had the hydrophilicity higher than PET-CTRL group; AAc-APP-1, AAc-APP-5, AAc-APP-10 and AAc-APP-15 groups (groups treated with acrylic acid plasma) had the hydrophilicity higher than that of PET-CTRL group (groups without any treatment) and that of Ar-APP-1, Ar-APP-5 and Ar-APP-10 groups (groups treated with argon plasma).

The change of hydrophilicity of AAc-APP-1, AAc-APP-5, AAc-APP-10 and AAc-APP-15 groups (groups treated with acrylic acid plasma) was further compared. Please refer to AAc-APP-1 group, AAc-APP-5 group and AAc-APP-10 group. As the plasma treatment time was increased from 1 s to 10 s, the hydrophilicity gradually increased. Furthermore, please refer to AAc-APP-10 group and AAc-APP-15 group. When the plasma treatment time was increased from 10 s to 15 s, there was no significant difference in hydrophilicity. That is, compared with AAc-APP-15 group, AAc-APP-10 group could achieve the hydrophilicity similar to that of AAc-APP-15 group using a shorter plasma treatment time.

3. Surface Stability Test

As the surface hydrophilicity test of point 2 mentioned above, each of the polymer layer or the modified polymer layers manufactured according to the conditions in Table 1 was placed for 7 days and 21 days, and the water contact angle of each group was also measured on different days. According to the change of the water contact angle, the surface stability of the hydrophilicity of each group was compared. Please refer to FIG. 3B, demonstrating the result of each group that the value was calculated after three repeated times.

Figure 3B:
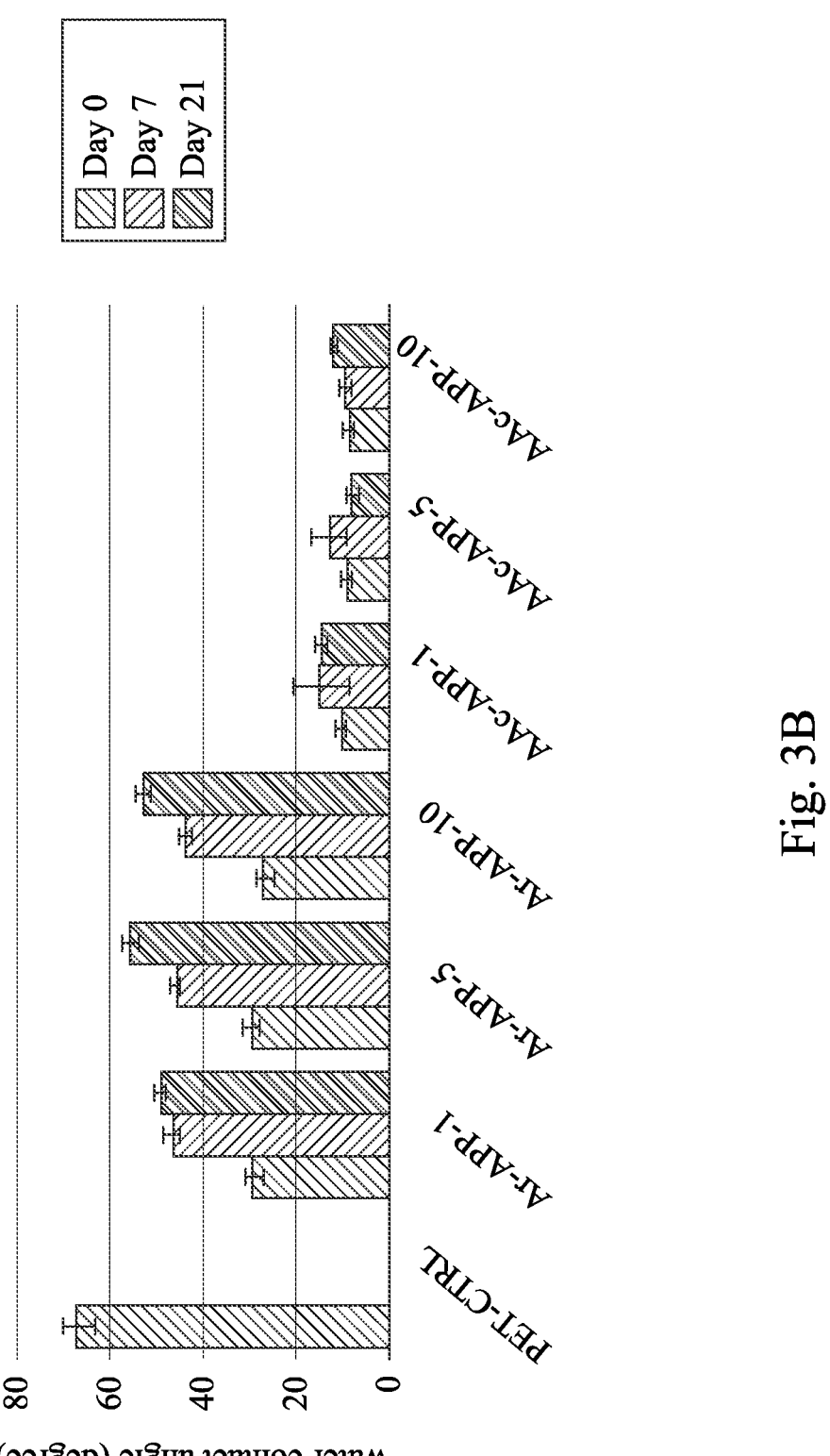
FIG. 3B depicts a comparison figure of contact angles between the modified polymer layer and the modified polymer layers obtained by the different manufacturing conditions when left for different days.

FIG. 3B demonstrated that the surface contact angles of Ar-APP-1, Ar-APP-5 and Ar-APP-10 groups (groups only treated with argon plasma) gradually increased as time increased (the surface hydrophilicity gradually decreased); AAc-APP-1, AAc-APP-5, AAc-APP-10 and AAc-APP-15 groups (groups treated with acrylic acid plasma) represented no significant change of water contact angle even after 21 days of placement, indicating that no difference of surface hydrophilicity was present. That is, the surface hydrophilicity of the groups of AAc series (groups treated with acrylic plasma) was not affected even if the groups of AAc series were left for 21 days. The surface stability of the groups of AAc series was better than that of the groups of Ar series.

Example 2, Cell Viability Test of Modified Polymer Layer Modified by Hydroxyapatite According to the groups shown in Table 2, the cell viability test was performed respectively.

The steps of the cell viability test were listed as follows: first, the osteoprogenitor cells (MC3T3-E1 cells) were cultured for three days, and the cells were collected in DMEM (Dulbecco's modified Minimal Essential Medium) at a state that the culture plate was about 80% covering. Further, 100 $\mu L$ DMEM containing the cells (the cell concentration was $1 \times 10^5$ cells/ml) and the polymer layer or the modified polymer layers in Table 2 were added into the wells of the 96-well plate, and the cell viability of each group on the $1^{st}$ day, the $3^{rd}$ day and the $5^{th}$ day was determined respectively, in which DMEM of the group to be tested on the $5^{th}$ day would be replaced once on the $3^{rd}$ day.

The assay method of cell viability included the following steps: first, after sucking DMEM from the wells, 100 $\mu L$ DMEM and 10 $\mu L$ cell counting reagent (Cell Counting Kit-8; CCK-8 reagent) were added. After culturing the cells in the condition of 37° C. and 5% $CO_2$ for 1 hr, the absorbance value at a wavelength of 450 nm was detected. Furthermore, the absorbance of the control group without addition of the polymer layer was calculated as cell viability of 100%, which was used as a benchmark to generate the cell viability of each group. Please refer to FIG. 3C, demonstrating the result of each group that the value was calculated after three repeated times.

TABLE 2

| Group | Name | Polymer Layer | Treatment Time of Argon Plasma (s) | Treatment Time of Acrylic Acid Plasma (s) | Alternative Immersion Method |
|---|---|---|---|---|---|
| Control | | — | — | — | — |
| Comparison | PET-CTRL | V | — | — | — |
| | PET-HAp | V | — | — | V |
| | Ar-APP-1 | V | 1 | — | V |
| Example | AAc-APP-1 | V | — | 1 | V |
| | AAc-APP-5 | V | — | 5 | V |
| | AAc-APP-10 | V | — | 10 | V |

The result of FIG. 3C demonstrated that there was no significant difference in the cell viability of each group on the $1^{st}$ day and the 3 rd day. However, on the $5^{th}$ day, the cell viability of AAc-APP-10 group (the group treated with acrylic acid plasma for 10 s) was significantly higher than that of other groups. The modified polymer layer of AAc-APP-10 group exhibited the best cell viability.

Although the disclosure has been disclosed in the above embodiments, it is not intended to limit the disclosure, and it is to be understood that those skilled in the art can make various changes and modifications without departing from the spirit and scope of the disclosure. The scope of protection of the present disclosure is subject to the definition of the scope of claims.

What is claimed is:

1. A manufacturing method of a modified polymer layer modified by hydroxyapatite, comprising following steps:
   (a) providing a polymer layer;
   (b) plasma-activating acrylic acid using an atmospheric cold plasma device comprising a plasma treatment zone to modify a surface of the polymer layer to obtain an acrylic-modified polymer layer, wherein the plasma treatment zone includes a V-shaped hollow tube and a hollow metal electrode accommodated in the V-shaped hollow tube;
   (c) immersing the acrylic-modified polymer layer in a first solution containing calcium ions to obtain a calcium-containing modified layer; and
   (d) immersing the calcium-containing modified layer in a second solution containing phosphate salt to obtain a modified polymer layer modified by the hydroxyapatite.

2. The manufacturing method of the modified polymer layer modified by the hydroxyapatite of claim 1, wherein the step (b) comprises introducing the acrylic acid and argon gas into the hollow metal electrode accommodated in a first hollow element of the V-shaped hollow tube, thereby generating an acrylic acid plasma from a bottom opening of the V-shaped hollow tube to modify the surface of the polymer layer.

3. The manufacturing method of the modified polymer layer modified by the hydroxyapatite of claim 2, wherein the step (b) further comprises modifying the surface of the polymer layer by using a needle-shaped metal electrode accommodated in a second hollow element of the V-shaped hollow tube, wherein the first hollow element intersects with the second hollow element to form the bottom opening.

4. The manufacturing method of the modified polymer layer modified by the hydroxyapatite of claim 1, wherein the step (b) comprises plasma-activating the acrylic acid at a temperature of from 25° C. to 70° C.

5. The manufacturing method of the modified polymer layer modified by the hydroxyapatite of claim 1, wherein the step (b) comprises plasma-activating the acrylic acid with a current of from 10-5 A to 1 A.

6. The manufacturing method of the modified polymer layer modified by the hydroxyapatite of claim 1, wherein the step (b) comprises modifying the surface of the polymer layer for 0.5 s to 20 s.

7. The manufacturing method of the modified polymer layer modified by the hydroxyapatite of claim 1, wherein in the step (c), a concentration of the calcium ions in the first solution is from 0.1 M to 0.5 M, and in the step (d), a concentration of the phosphate salt in the second solution is from 0.05 M to 0.3 M.

8. The manufacturing method of the modified polymer layer modified by the hydroxyapatite of claim 1, wherein the first solution in the step (c) is calcium nitrate tetrahydrate solution, and the second solution in step (d) is diammonium hydrogen phosphate solution.

9. The manufacturing method of the modified polymer layer modified by the hydroxyapatite of claim 1, wherein an immersion time of the step (c) or the step (d) is from 0.25 hr to 1 hr.

10. The manufacturing method of the modified polymer layer modified by the hydroxyapatite of claim 1, further comprising repeating the step (c) and the step (d), wherein the modified polymer layer is alternately immersed in the first solution and the second solution for 1 cycle to 5 cycles.

* * * * *